United States Patent [19]
Gupta et al.

[11] Patent Number: 6,125,789
[45] Date of Patent: Oct. 3, 2000

[54] INCREASING THE SENSITIVITY OF AN IN-SITU PARTICLE MONITOR

[75] Inventors: Anand Gupta, Phoenix, Ariz.; Vijay Parkhe, Sunnyvale, Calif.

[73] Assignee: Applied Materials, Inc., Santa Clara, Calif.

[21] Appl. No.: 09/016,241

[22] Filed: Jan. 30, 1998

[51] Int. Cl.[7] .............................. C23C 16/00; H05H 1/00
[52] U.S. Cl. .................. 118/723 E; 118/723 FI; 156/345
[58] Field of Search .................. 156/345; 118/723 E, 118/723 FI, 723 A, 723 VE

[56] References Cited

U.S. PATENT DOCUMENTS

| | | | |
|---|---|---|---|
| 4,626,447 | 12/1986 | Doehler et al. | 118/723 E |
| 5,083,865 | 1/1992 | Kinney et al. | 356/338 |
| 5,255,089 | 10/1993 | Dybas et al. | 358/101 |
| 5,298,720 | 3/1994 | Cuomo et al. | 219/121.43 |
| 5,328,555 | 7/1994 | Gupta | 156/643 |
| 5,347,138 | 9/1994 | Aqui et al. | 250/573 |
| 5,456,796 | 10/1995 | Gupta et al. | 156/643.1 |
| 5,474,649 | 12/1995 | Kava et al. | 156/345 |
| 5,494,523 | 2/1996 | Steger et al. | 118/723 E |
| 5,529,657 | 6/1996 | Ishii | 118/723 E |
| 5,552,124 | 9/1996 | Su | 156/345 |
| 5,605,576 | 2/1997 | Sasaki et al. | 118/723 FI |
| 5,733,405 | 3/1998 | Taki et al. | 118/723 FI |

FOREIGN PATENT DOCUMENTS

| | | | |
|---|---|---|---|
| 0 497 563 A2 | 8/1992 | European Pat. Off. | H01L 21/306 |
| 0 574 859 A1 | 12/1993 | European Pat. Off. | H01J 37/32 |
| 6-124902 | 5/1994 | Japan | H01L 21/205 |

OTHER PUBLICATIONS

G. Praburam et al., "Observations of Particle Layers Levitated in a Radio–frequency Sputtering Plasma," *Department of Physics and Astronomy*, The University of Iowa, Iowa City, Iowa 52242, pp. 3137–3145 (1994). (no month).

A. Gupta et al., "Particle Reduction Usig Plasma Management," *Corporate Microcontamination*, pp. 1–2. (no month) (no year).

K. Donohoe, "Electron Motion in the Precision 5000 Etch: Magnetic Field Effects," *Applied CVD and ETCH Technologies in Review*, pp. 6–7 (1990). (no month).

G. Praburam et al., "Evolution of a Particulate Cloud in an RF Plasma," *Department of Physics*, The University of Iowa, Iowa City, IA 52242, pp. 1–6. (no month, no year).

Dr. W.H. Class, "Advances in Thin Film Technology Sputtering and Etching," *The Book of Basics*, HB 1–18–1–19, HB 1–39–1–44 (1984). (no month).

*Primary Examiner*—Shrive Beck
*Assistant Examiner*—Parviz Hassanzadeh
*Attorney, Agent, or Firm*—Townsend & Townsend & Crew

[57] ABSTRACT

A method and apparatus for increasing the sensitivity of an in situ particle monitor. A light scattering technique, preferably using laser light, is employed to monitor particle concentrations within the processing chamber of a plasma-based substrate processing system. Particle concentrations are increased in the light field of the sensor by creating an electric or magnetic field in the processing chamber to concentrate the particles suspended therein.

31 Claims, 8 Drawing Sheets

INCREASING THE SENSITIVITY OF AN IN-SITU PARTICLE MONITOR

BACKGROUND OF THE INVENTION

This invention relates to a method for monitoring particles in a plasma processing chamber.

Since semiconductor devices were first introduced several decades ago, the features sizes of the devices created with these thin films have decreased dramatically in size. During that time, integrated circuits have generally followed the two year/half-size rule (often called "Moore's Law"), which states that the number of devices that will fit on a chip will double every two years. Today's semiconductor fabrication plants routinely produce devices with feature sizes of 0.5 μm or even 0.35 μm, and tommorrow's plants will be producing devices with even smaller feature sizes.

Even as feature sizes have diminished, die sizes have increased. Smaller feature sizes and larger die sizes used in today's semiconductor devices have effectively created a larger target that is susceptible to damage by smaller particles. Because both of these effects reduce yield, particle contamination has become of increasing concern. The presence of particles during deposition of etching of thin films can cause voids, dislocations, or shorts, which adversely affect performance and reliability of the devices fabricated.

The problem of contaminant particles was addressed initially by improving the quality of clean room ambients and employing automated equipment to handle materials and semiconductor substrates. Cleaning of substrate surfaces was also improved. These improvements have reduced the number of particles that exist in the processing ambient or on the substrate surface during the processing cycle. However, particles may be generated inside the process chamber by sources such as the processing materials employed, mechanical contact (e.g., between surfaces in robotic equipment during transfer operations), electrical arcs, and the like.

In particular, during plasma-based substrate processing (e.g., physical-vapor deposition (PVD), plasma-enhanced chemical vapor depositions (PECVD), high-density plasma CVC (HDP-CVD), and similar processes), numerous fragments of various kinds and generated from the process gases employed, including ions, electrons, particles, and the like. The fragments can combine to form particles having small negative charges, i.e., on the order of $10^4$ negative elementary charges (an elementary charge is the charge possessed by a single electron). Additionally, residues may accumulate on the processing chamber's interior surfaces during plasma-based substrate processing operations. These residues may include substances such as polymers and compounds formed by the reaction of process gases and the chamber. Stress, such as that due to thermal cycling and the like, may subsequently cause these films to fracture and dislodge from the surfaces on which they have formed, thereby generating particles. Particles may also be generated within the processing chamber during substrate transfer operations, by friction between components, by differences in thermal expansion coefficients, and other sources.

The prior art teaches various techniques for reducing the deposition of particles onto substrates during processing and techniques for removing particles between process steps. However, despite the reduced particle counts provided by these techniques, there remain the need to monitor particle concentrations because particles cannot be completely eliminated from processing chambers. Thus, depending on the process, a processing chamber must be opened and mechanically cleaned (as by wiping) at some point. Because such cleaning operations are disruptive to throughput, they should be performed as infrequently as possible. On the other hand, allowing a chamber to become overly susceptible to contaminating particles can adversely affect yield. Accurate monitoring of particle counts allows optimization of the frequency with which chambers are dismantled for cleaning and also permits the detection of catastrophic failures that might not otherwise be detected as rapidly.

Several types of particle monitoring systems are in use in the semiconductor industry. For example, one type of system monitors particles in the exhaust gas stream by shining a high-intensity laser beam across the gas stream, and detecting scattered light. The amount of scattered light provides a measure of the particle concentration in the exhaust gas, and by implication, a measure of the particle counts within the reaction chamber.

While exhaust gas monitors are presumably effective, the information they provide is second-hand. Preferably, those who operate substrate processing equipment would like to directly measure the particulate concentration within a processing chamber using an in situ technique. This may be done in a manner similar to the aforementioned particle monitoring technique, in which the laser light is sent through the chamber in the space above the substrate being processed. A technique of this sort is described in U.S. Pat. No. 5,328,555, entitled "Reducing Particulate Contamination During Semiconductor Device Processing," issued to A. Gupta. The U.S. Pat. No. 5,328,555 patent is assigned to Applied Materials, Inc., the assignee of the present invention, and is hereby incorporated by reference in its entirety.

The U.S. Pat. No. 5,328,555 patent describes a particle concentration measurement system employing an in situ technique. A laser light-scattering system described therein permits operations such as viewing and measuring particle concentrations within the system's processing chamber. The measurement system's laser is connected to a scanner by a fiber optic cable. The fiber optic cable can be mounted in a laser holder attached to a vertical shaft supported on a rotational base. Any laser whose radiation may be scattered by the particles existing in the processing chamber may be sued.

The scanner is mounted on a holder attached to an adjustable verticle stage to permit the illuminated volume to be positioned at varying heights above the substrate being processed. The laser and scanner slide on an optical rail situated parallel to a chamber viewport. This arrangement provides adjustment in the X, Y, and Z directions. The consistency of the laser light field is controlled by a frequency generator input. It is this oscillation that produces the laser light field. The amount of oscillation (i.e., the size of the laser light field) can be varied by varying the amplitude of the voltage input to the scanner, with a DC offset controlling the starting position of the laser light field's extent.

The laser light field illuminates particles within the processing chamber. Laser light in this field is scattered by these particles, and is then detected by a detection device such as a camera. The camera is configured to provide various focal lengths by adjustment of the viewing distance from a second chamber viewport. Laser light scattered from the particles lying within the camera's field of view may then be accounted for in a variety of ways, such as by display on a monitor, which permits viewing of the particles or measurement of the scattered light's intensity.

Undoubtedly, feature size will continue to decrease, driving the need for further reductions in particle concentrations to maintain yield. Additionally, smaller feature sizes will mean increased sensitivity to defects caused by particles, reducing the particle size necessary to cause a defect and increasing the amount of damage done by a given particle. Thus, even if an in situ technique is employed, accurate measurement of these particle concentrations may prove difficult, due to the particle size and reduced concentrations which must be accurately detected. What is therefore needed is a method of increasing the sensitivity of both existing and future in situ particle concentration sensing techniques.

SUMMARY OF THE INVENTION

The present invention is directed to a method and apparatus for increasing the sensitivity of an in situ particle monitor. An optical technique, preferably based on the scattering of laser light, is employed to monitor particle concentrations within the processing chamber of a plasma-based substrate processing system (e.g., PVD or PECVD system). Alternatively, other methods of detecting particles by their interaction with light (e.g., changes in polarization) may be employed by the present invention. Particle concentrations are increased in the light field of the sensor by creating an electric or magnetic field in the processing chamber to concentrate the particles suspended therein.

According to the method of the present invention, an in situ particle monitoring system is provided for monitoring a concentration of particles in a processing chamber of a substrate processing system. The monitor includes a light source for directing light into a gas-containing region of the processing chamber and for illuminating particles suspended in the gas-containing region; an optical detector for monitoring the concentration of the particles by detecting light after it interaction with the particles (e.g., by absorption or reflection); optically transparent windows in the processing chamber's wall, for providing optical access to the gas-containing region for the light source and the optical detector; and a particle concentrator for concentrating the particles in a volume, the volume being in an optical line with the light source and the optical detector. The light source is preferably a laser, but may be any suitable source of light.

The particle concentrator may use either an electric or a magnetic field to concentrate the particles, which acquire a small charge when immersed in the plasma within the processing chamber. An electric field may be created by creating a disturbance in the plasma, thus using energy from the plasma. A magnetic field may be created using an externally powered source, such as a toroidal electromagnet.

According to the method of the present invention, another aspect of the present invention is a method for improving the sensitivity of the light-scattering particle concentration monitor by increasing the concentration of particles in a volume illuminated by a light source. This may be done by first creating a plasma within a processing chamber of a substrate processing system and then trapping particles using an electric field, thereby causing a concentration of the particles in conformance with the electric field. Alternatively, a magnetic field may be applied with similar results. Particle concentration may then be more easily monitored using the light-scattering particle concentration monitor. A combination of an electric field and a magnetic field may also be used to trap the particles.

A further understanding of the nature and advantages of the present invention may be realized by reference to the remaining portions of the specification and the drawings.

DETAILED DESCRIPTION OF THE INVENTION

I. Introduction

The present invention is a method and apparatus for improving the sensitivity of in situ monitoring of particle concentrations in a plasma-based substrate processing system. The present invention concentrates particles suspended in a plasma by the use of an electric or magnetic field, allowing easier detection using an in situ light scattering technique. Particle concentration is increased by increasing the probability of a given particle passing through or remaining in the volume illuminated by the light source. The present invention can be practiced in substrate processing chambers of conventional design.

II. An Exemplary CVD System

Figure 1A:
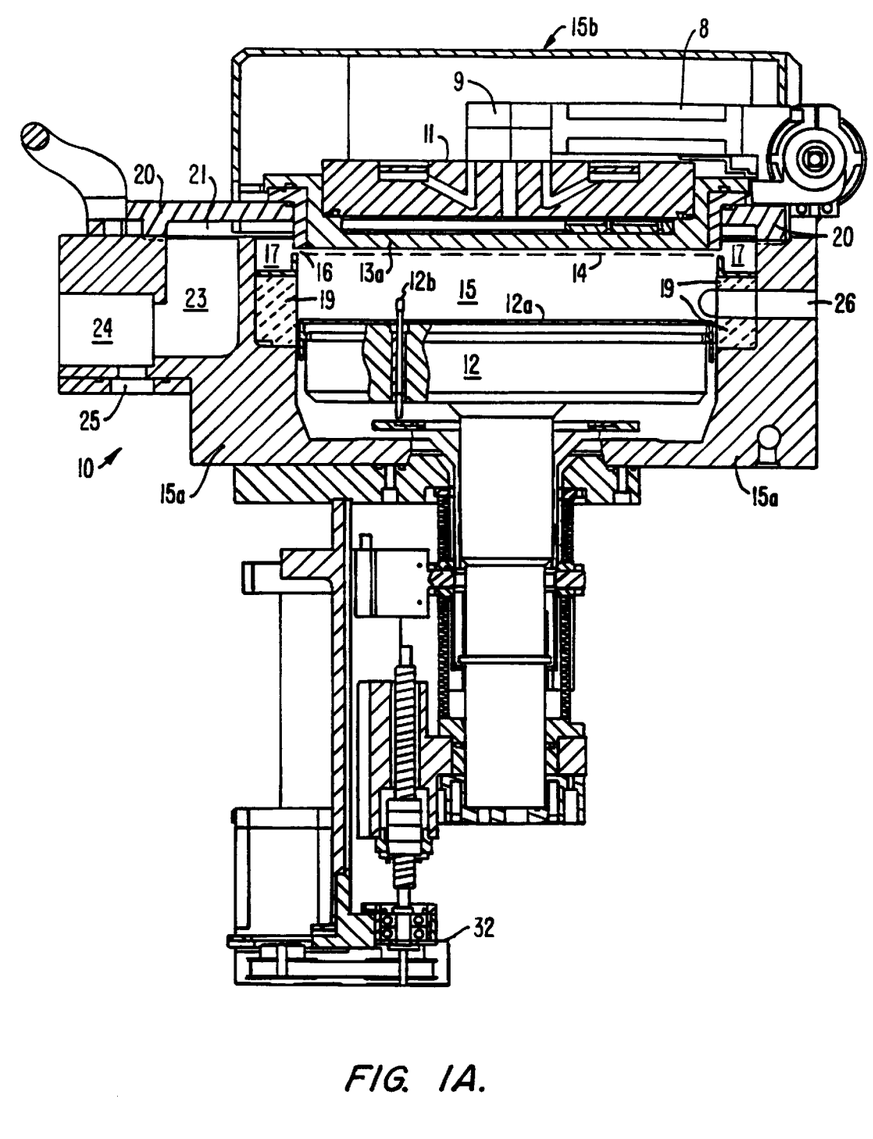
FIGS. 1A and 1B are vertical, cross-sectional views of one embodiment of a chemical vapor deposition (CVD) apparatus according to the present invention.
Figure 1B:
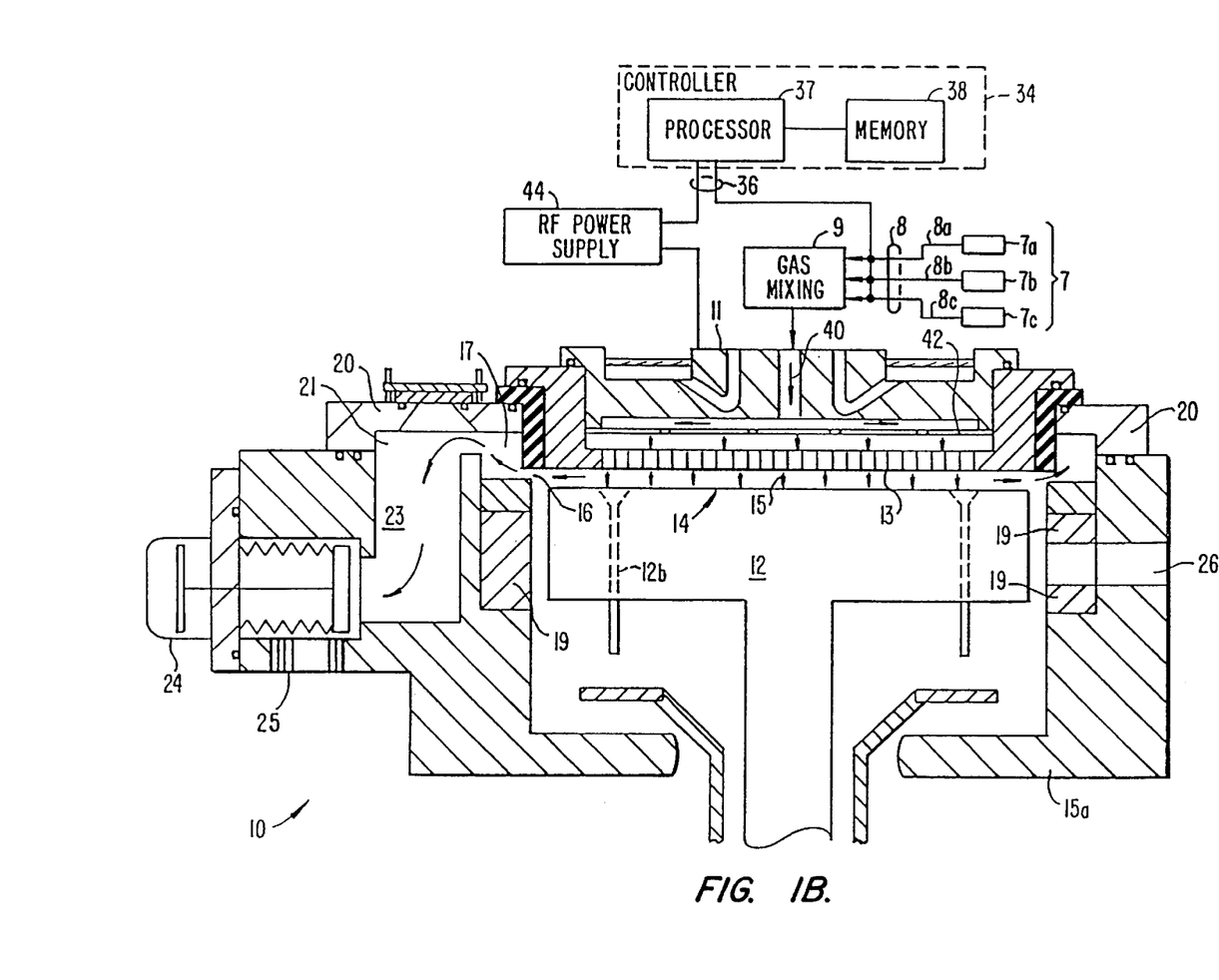
Figure 1C:
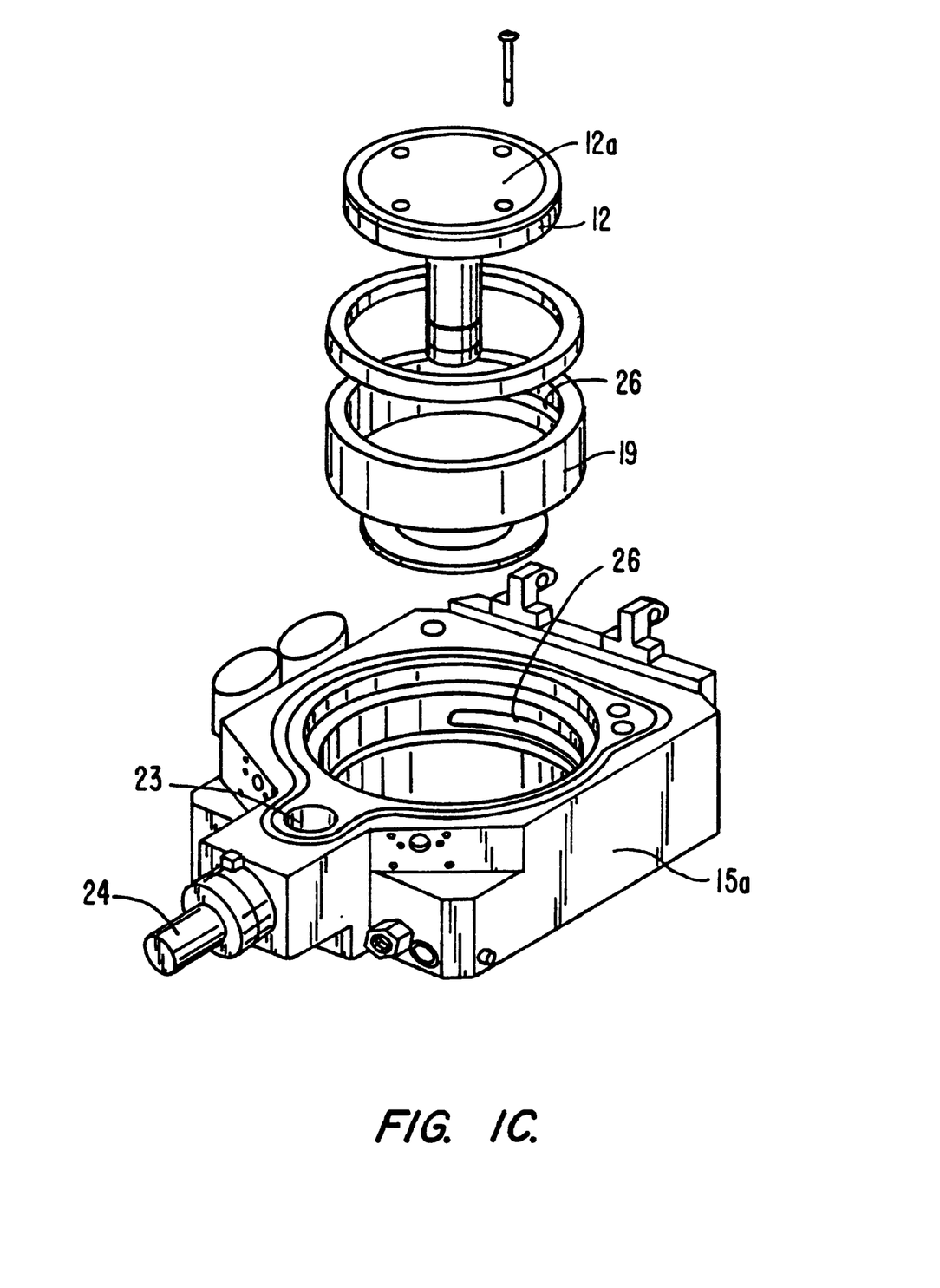
FIGS. 1C and 1D are exploded perspective view of parts of the CVD chamber depicted in FIG. 1A.

One suitable CVD system in which the present invention can be practiced is shown in FIGS. 1A and 1B, which are vertical, cross-sectional views of a chemical vapor deposition (CVD) system 10, having a vacuum or processing chamber 15 that includes a chamber wall 15a and chamber lid assembly 15b. Chamber wall 15a and chamber lid assembly 15b are shown in exploded, perspective views in FIGS. 1C and 1D.

CVD system 10 contains a gas distribution manifold 11 for dispersing process gases to a substrate (not shown) that rests on a heated pedestal 12 centered within the process chamber. During processing, the substrate (e.g., a semiconductor wafer) is positioned on a flat (or slightly convex) surface 12a of pedestal 12. Pedestal 12 can be controllably moved between a lower loading/off-loading position (depicted in FIG. 1A) and an upper processing position (indicated by dashed line 14 in FIG. 1A and shown in FIG. 1B), which is closely adjacent to manifold 11. A centerboard (not shown) includes sensors for providing information on the position of the substrates.

Deposition and carrier gases are introduced into chamber 15 through perforated holes 13b (FIG. 1D) of a conventional flat, circular gas distribution faceplate 13a. More specifically, deposition process gases flow into the chamber through manifold 11 (indicated by arrow 40 in FIG. 1B), through a conventional perforated blocker plate 42 and then through holes 13b in gas distribution faceplate 13a. Before reaching the manifold, deposition, and carrier gases are input from gas sources 7 through gas supply lines 8 into a mixing system 9 where they are combined and then sent to manifold 11. Generally, the supply line for each process gas includes (i) several safety shut-off valves (not shown) that can be used to automatically or manually shut off the flow of process gas into the chamber, and (ii) mass flow controllers (also not shown) that measure the flow of gas through the supply line. When toxic gases are used in the process, the several safety shut-off valves are positioned on each gas supply line in conventional configurations.

The deposition process performed in CVD system 10 can be either a thermal process or a plasma-enhanced process. In a plasma-enhanced process, a radio frequency (RF) power supply 44 applies electrical power between gas distribution faceplate 13a and pedestal 12 so as to excite the process gas mixture to form a plasma within the cylindrical region between faceplate 13a and pedestal 12. (This region will be referred to herein as the "reaction region"). Constituents of the plasma react to deposit a desired film on the surface of the substrate supported on pedestal 12. RF power supply 44 is a mixed-frequency RF power supply that typically supplies power at a high RF frequency (RF1) of 13.56 MHz and at a low RF frequency (RF2) of 360 KHz to enhance the decomposition of reactive species introduced into chamber 15.

During a deposition process, the plasma heats chamber 15, including that portion of wall 15a surrounding exhaust passageway 23 and shut-off valve 24. When the plasma is not turned on, a hot liquid is circulated through wall 15a to maintain chamber 15 at an elevated temperature. Fluids used to heat wall 15a include the typical fluid types, i.e., water-based ethylene glycol or oil-based thermal transfer fluids. This heating beneficially reduces or eliminated condensation of undesirable reactant products and improves the elimination of volatile products of the process gases and other contaminants that might contaminate the process if they were to condense on the walls of cool vacuum passages and migrate back into the processing chamber during periods of no gas flow.

The remainder of the gas mixture that is not deposited in a layer, including reaction products, is evacuated from the chamber by a vacuum pump (not shown). Specifically, the gases are exhausted through an annular, a slot-shaped orifice 16 surrounding the reaction region and into a annular exhaust plenum 17. Orifice 16 and plenum 17 are defined by the gap between the top of wall 15a (including an upper dielectric lining 19 on wall 15a) and the bottom of circular chamber lid 20. The 360 circular symmetry and uniformity of orifice 16 and plenum 17 are important to achieving a uniform flow of process gasses over the substrate so as to deposit a uniform film on the substrate.

From exhaust plenum 17, the gases flow underneath a lateral extension portion 21 of exhaust plenum 17, through a downward-extending gas passage 23, past a vacuum shut-off valve 24 (whose body is integrated with the lower portion of wall 15a), and into exhaust outlet 25 that connects to an external vacuum pump (not shown) through a foreline (also not shown).

The substrate support platter of pedestal 12 (preferably aluminum) is heated using a double full-turn single-loop embedded heater element configured to form parallel concentric circles. An outer portion of the heater element runs adjacent to a perimeter of the support platter, while an inner portion runs on the path of a concentric circle having a smaller radius. The wiring to the heater element passes through the stem of pedestal 12.

Typically, any or all of the chamber lining, gas inlet manifold faceplate, and various other reactor hardware are made out of material such as aluminum or anodized aluminum. An example of such a CVD apparatus is described in U.S. Pat. No. 5,558,717 entitled "CVD Processing Chamber," issued to Zhao et al. The U.S. Pat. No. 5,558,717 patent is assigned to Applied Materials, Inc., the assignee of the present invention, and is hereby incorporated by reference in it entirety.

A lift mechanism and motor 32 raises and lowers pedestal 12 and its substrate lift pins 12b substrates are transferred into and out of the body of the chamber by a robot blade (not shown) through an insertion/removal opening 26 in the side of chamber 15. Motor 32 raises and lowers pedestal 12 between a processing position 14 and a lower, substrate-loading position. Motor 32, valves or flow controller connected to supply lines 8, gas delivery system, throttle valve, RF power supply 44, and chamber and substrate heating systems are all controlled by a system controller 34 over control lines 36, of which only some are shown. Controller 34 relies on feedback from optical sensors to determine the position of movable mechanical assemblies such as the throttle valve and susceptor that are moved by appropriate motors under the control of controller 34.

In a preferred embodiment, the system controller includes a hard disk drive (memory 38), a floppy disk drive and a processor 37. Processor 37 contains a single-board computer (SBC), analog and digital input/output boards, interface boards and stepper motor controller boards. Various parts of CVD system 10 conform to the Verso Modular European (VME) standard that defines board, card cage, and connector dimensions and types. The VME standard also defines the bus structure having a 16-bit data bus and 24-bit address bus.

System controller 34 controls all of the activities of the CVD machine. The system controller executes system control software, which is a computer program stored in a computer-readable medium such as a memory 38. Preferably, memory 38 is a hard disk drive, but memory 38 may also be other kinds of memory. The computer program includes sets of instructions that dictate the timing, mixture of gases, chamber pressure, chamber temperature, RF power levels, susceptor position, and other parameters of a particular process. Other computer programs stored on other memory devices including, for example, a floppy disk or other another appropriate drive, may also be used to operate controller 34.

Figure 1D:
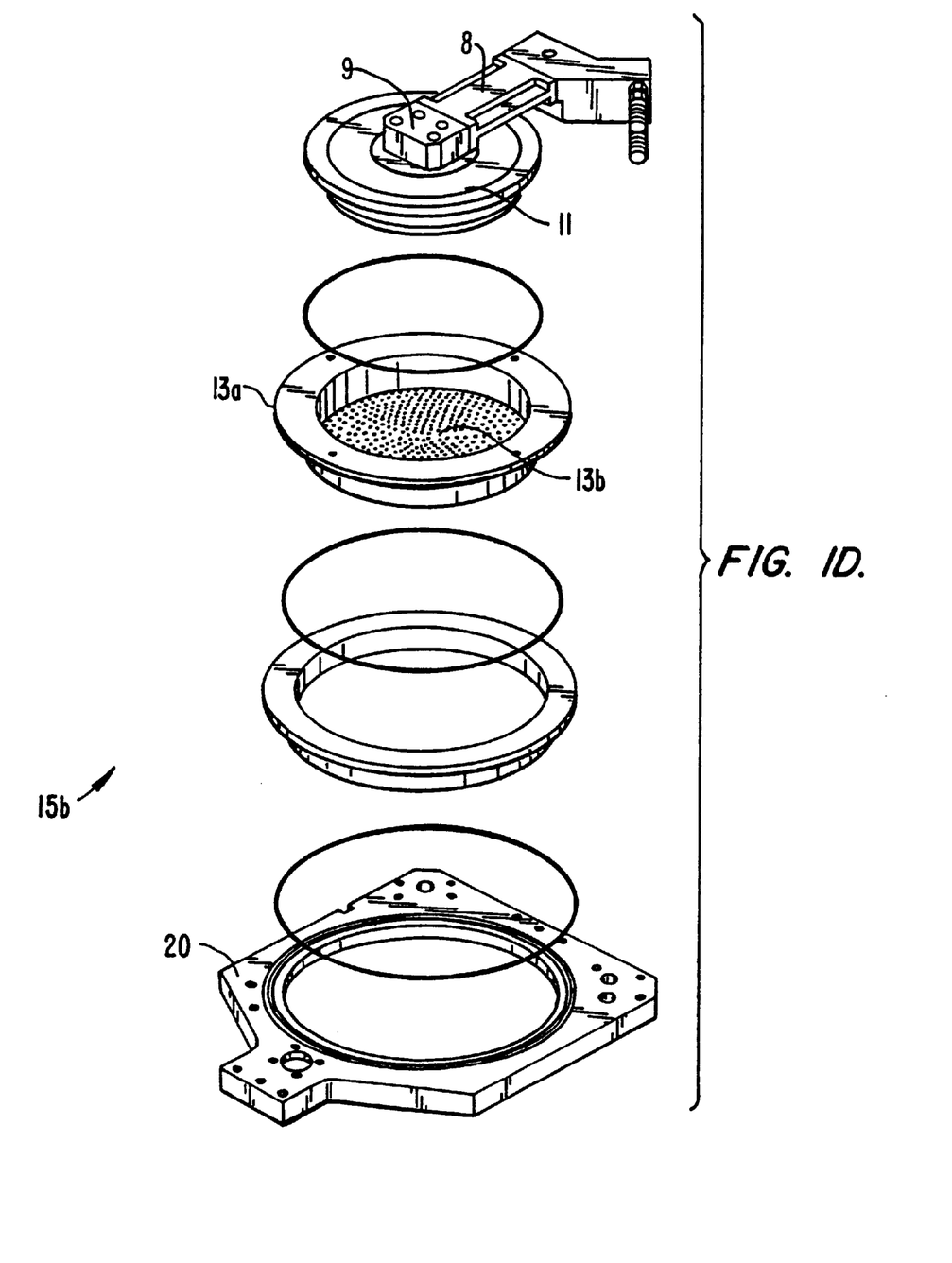
Figure 1E:
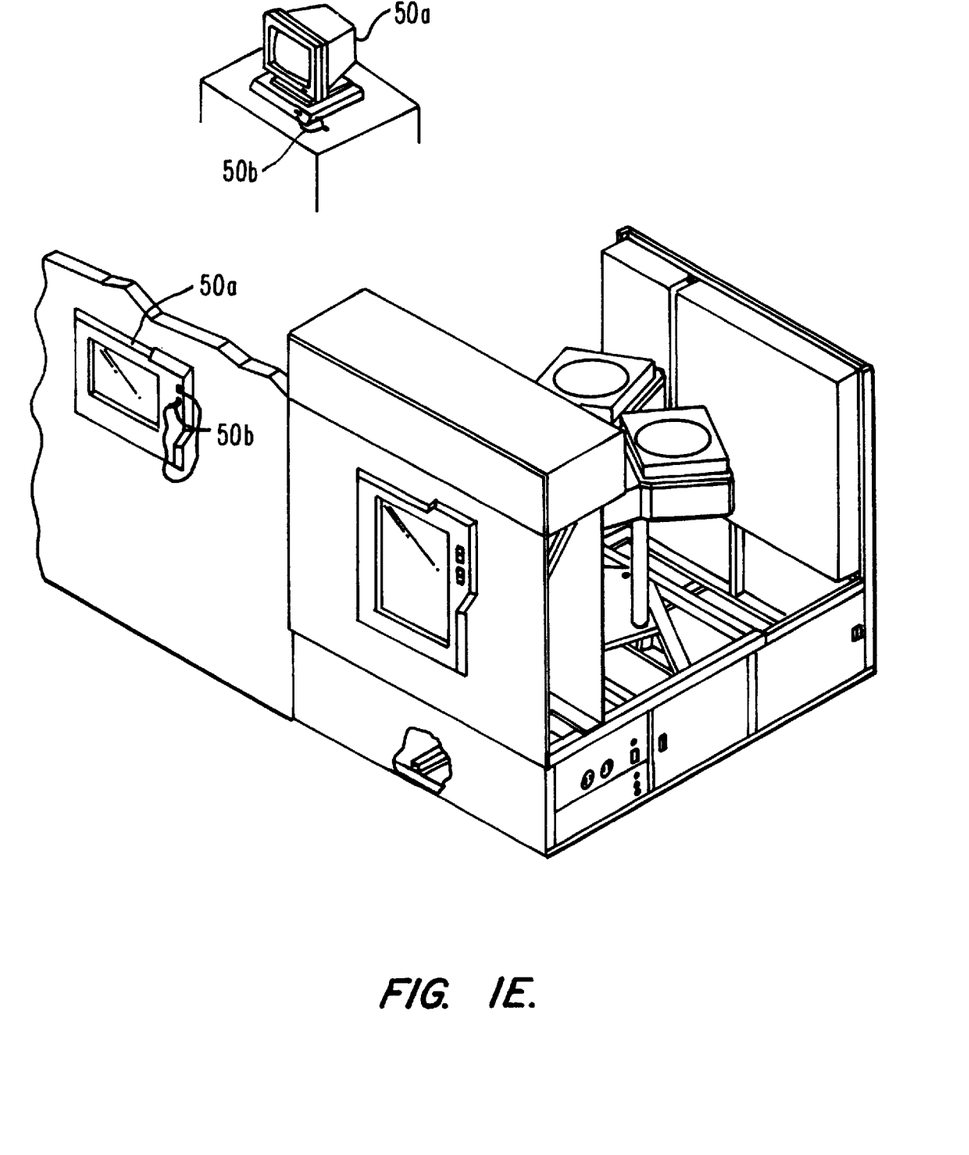
FIG. 1E is a simplified diagram of a system monitor and CVD system in a multichamber system, which may include one or more chambers.

The interface between a user and controller 34 is via a CRT display 50a and light pen 50b, shown in FIG. 1E, which is a simplified diagram of the system display and CVD system 10 in a substrate processing system that may include one or more chambers. In the preferred embodiment, two displays 50a are sued, one mounted in the clean room wall for the operators and the other behind the wall for the service technicians. Displays 50a simultaneously display the same information, but only one light pen 50b is enabled. A light sensor in the tip of light pen 50b detects light emitted by display 50a. To select a particular screen or function, the operator touches a designed area of the display's screen and pushes the button on pen 50b. the touched area changes its highlighted color, or a new menu or screen is displayed, confirming communication between the light pen and the display screen. Other devices, such as a keyboard, mouse, or other pointing or communication device, may be used instead of or in addition to light pen 50b to allow the user to communicate with controller 34.

The above reactor description is for illustrative purposes, and other semiconductor processing equipment such as PVD equipment, etching equipment, other plasma CVD equipment, or the like may benefit from the detection capabilities provided by the present invention. Additionally, variations of the above-described system, such as variations in susceptor design, heater design, RF power frequencies, location of RF power connections and other are possible. The enhancement in particle detection provided by the present invention is not limited to any specific apparatus or to any specific plasma excitation method.

III. Improving In Situ Particle Detection by the Method of the Present Invention As noted, particles generated within a substrate processing system are a serious problem due to the possibility of contamination and the resulting adverse affect on yield. While these particles may be detectable by laser light scattering (LLS) techniques, shrinking feature sizes demand greater sensitivity from such detection systems. The method and apparatus of the present invention provide such increased sensitivity in plasma-based substrate processing systems.

Figure 2:
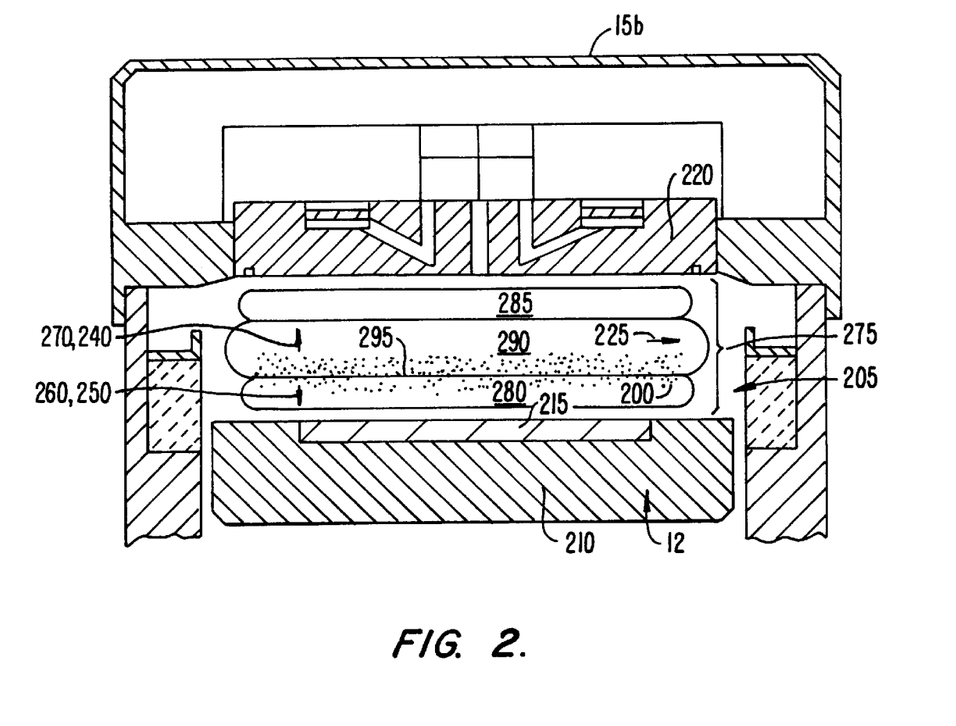
FIG. 2 is a simplified diagram of a plasma-based substrate processing system illustrating the various forces that may act upon particles suspended in a plasma in the processing chamber thereof.

Often, particles exist in the plasma generated in many types of common substrate processing systems. Particles in such plasmas are subject to a combination of electrical, collisional, gravitational, and other forces. These effects are shown in FIG. 2, which illustrates the forces experienced by particles 200 within a processing chamber 205, which corresponds to chamber 15 of FIG. 1A. Particles 200 range in diameter from a few nanometers to tens of micrometers.

Particles 200 are localized both vertically and horizontally by a variety of forces. Particles 200 are often localized in a circular disk, normally just above a substrate 215, and between a cathode 210 and an anode 220, which correspond to pedestal 12 and chamber lid assembly 15b of FIG. 1A, respectively. For simplicity, it is assumed that cathode 210 and anode 220 in FIG. 2 are positioned horizontally and that cathode 210 is below anode 220.

In the horizontal direction, particles 200 experience an outward force due to a viscous drag 225. Viscous drag 225 is caused by the flow of reactant and carrier gases, which normally enter processing chamber 205 via a central source above substrate 215 (e.g., by gas distribution faceplate 13a, as shown in FIGS. 1A and 1D), flow across substrate 215 radially and are evacuated at the edges of substrate 215 (e.g., via exhaust plenum 17, as shown in FIGS. 1A and 1B).

In the vertical direction, several forces act on particles 200. Because anode 220 is often cooler than cathode 210, a thermophoretic force 240 is exerted on particles 200. A thermophoretic force drives particles away from a hotter region and towards a colder region. In FIG. 2, this means that the particles are driven away from cathode 210 and towards anode 220. An ion drag force 250 and a gravitational force 260 oppose thermophoretic force 240. Gravitational force 260 exerts force toward cathode 210 (downward, in most substrate processing systems) simply due to the weight of particles 200. Ion drag force 250 is exerted on the particles by ions created in processing chamber 205 during substrate processing operations, which draw the particles toward cathode 210.

Finally, and electrostatic repulsive force 270 pushes particles 200 away from cathode 210 (upward, in most substrate processing systems). Particles 200 are forced away from cathode 210 because particles 200, when immersed in a plasma 275, acquire a small negative electrical charge, as discussed previously. Plasma 275, shown in FIG. 2 as including a first sheath 280, a second sheath 285, and a glow region 290, is the source of this charge. While gravitational force 260 tends to pull the particles toward cathode 210, electrostatic repulsive force 270, which is caused by first sheath 280, tends to push the particles away from cathode 210. Given the proper parameters, the particles will exhibit a tendency to remain between the center of glow region 290 and substrate 215, and near a boundary 295 between first sheath 280 and glow region 290. Thus, particles 200 will remain near the region about boundary 295 unless the aforementioned forces' net effect drives the particles to one of the electrodes or causes them to escape radially. Unfortunately, although they are not spread evenly throughout the volume of processing chamber 205 (which would be their minimum concentration), particles 200 may not be concentrated enough to permit their accurate detection for processes sensitive to lower particle concentrations and smaller particles.

Figure 3A:
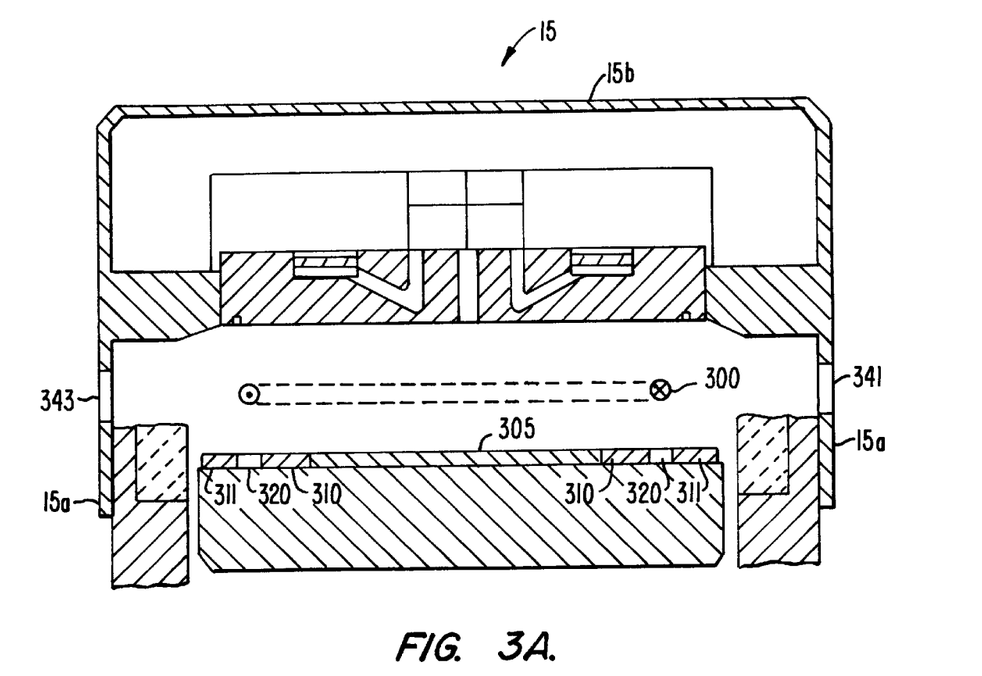
FIG. 3A is a simplified side view of a laser light-scattering particle monitor employing one embodiment of the present invention to improve the monitor's sensitivity.
Figure 3B:
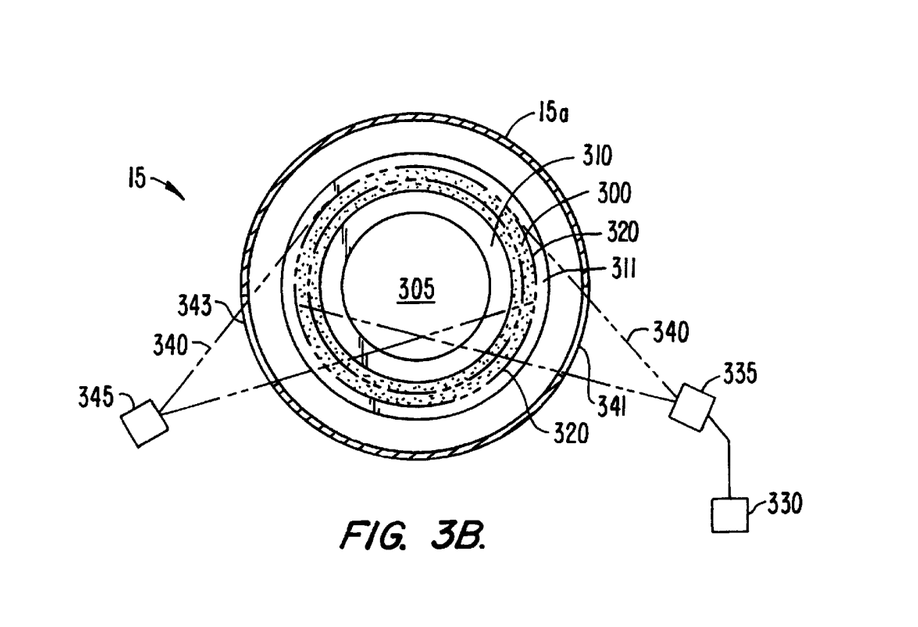
FIG. 3B is a simplified top view of a laser light-scattering particle monitor employing one embodiment of the present invention to improve the monitor's sensitivity.

FIGS. 3A (side view) and 3B (top view) illustrate one embodiment of the present invention that allows the detection of such particles. In this embodiment, particles 300 are concentrated into an annulus above a substrate 305 and below chamber lid assembly 15b (of FIG. 1A). particles 300 coalesce into an annulus as a result of the electric field created by metal spacing rings 310 and 311, and a dielectric ring 320, which are positioned concentrically around substrate 305. Dielectric ring 320 constructed from an insulator capable of withstanding the environmental extremes of a plasma-based process and one that will not significantly contribute to the particle concentration existing within the processing chamber, such as alumina, quartz, or aluminum nitride. As shown in FIGS. 3A and 3B, particles 300 are forced into an annulus. Once particles within processing chamber 15 (as in FIG. 1A) have coalesced into an annulus, their concentration is greater than in their previous (unconcentrated) state. A laser light scattering technique is then used to detect particles 300 forced into the volume of the annulus. Laser light from a laser 330 is directed through a scanner 335 that spreads the laser light throughout a volume, as previously described. The laser light is then directed along a light path 340, entering chamber 15 through a first window 341 in chamber wall 15a, scattering off of particles 300 and exiting through a second window 343. The scattered laser light is then detected using a photosensor apparatus 345.

While two windows, first window 341 and second window 343, are provided for laser light to enter and exit, respectively, chamber 15 in FIGS. 3A and 3B, these two windows could be combined into a single window (not shown). This single window might extend from the position of first window 341 to that of second window 343. Alternatively, a single window might simply extend around the entire circumference of chamber 15 at the level of the two windows. With suitable modifications to chamber wall 15a (i.e., the addition of chamber viewports), the present invention may thus be practiced in a substrate processing system such as chemical vapor deposition system 10.

Alternatively, the present invention may use particle sensing techniques such as polarization detection, in which the interaction between the impinging light and the concentrated particles alters the light's polarization. Using a polarization detection technique, the size of the particles detected may also be estimated.

Sensing is performed by measuring the amount of laser light scattered off the particles within chamber 15. As noted, advances in substrate processing technology will continue to reduce the number of particles existing within chamber 15, while also necessitating the detection of smaller particles. The present invention provides improved detection of lower particle concentrations and smaller particles by increasing particle concentration in the volume illuminated by light path 340. Thus, for a given number of particles within chamber 15, more particles 300 will be situated in light path 340 to scatter the laser light supplied than would otherwise be the case. The output from photosensor apparatus 345 may then be used to determine when particle concentrations have risen to an unacceptable level. For example, this output may be monitored constantly (as by a chart recorder) to track particle concentrations for purposes such as yield analysis.

Additionally, the output may be monitored with respect to a threshold value, beyond which particle concentrations may not be allowed to rise. Upon the output from photosensor apparatus 345 attaining or exceeding this value, a cleaning operation would be performed to remove the excess particles. For example, the use of a threshold is important where the particle concentration increases over the course of processing several substrates. For a certain number of substrates, the particle concentration will remain fairly stable at a given (acceptable) level. However, at some point, processing residues accumulate in the processing chamber to the point where they cause the particle concentration therein to rise to unacceptable levels. When this occurs, one or more cleaning operations must be performed. An LLS system according to the present invention can be configured to detect such a condition by setting the threshold value to an appropriate level. Such a system would then indicate an unacceptable particle concentration by an alarm, an indicator on a control display, or a similar technique.

In this embodiment, particles 300 are concentrated in an annulus above dielectric ring 320. Particles 300 are concentrated in this manner because of the electropotential well that exists above dielectric ring 320. A volume having a current density lower than that of the surrounding space is referred to as an electropotential well because its charge potential is below that of the surrounding space. The electropotential well is formed in the following manner. The current density (e.g., between the electrodes of the apparatus in FIG. 3A) is determined, in part, by the RF impedance of the materials used in fabricating each electrode. Each material's RF impedance is, in turn, a function of the material's permittivity ($\epsilon$). The higher the material's permittivity, the greater the material's RF impedance and the lower the current density between that material and the opposing electrode. Current density gradients exist between contiguous volumes having different current densities. Such gradients tend to force negatively-charged particles (e.g., the particles in the plasma within chamber 15) away from the volumes having higher current density, and into the volumes having lower current density.

The current density between each one of the rings in FIGS. 3A and 3B, and gas distribution faceplate 13a thus depends, in part, on the materials from which each ring is fabricated. Because dielectric ring 320 is fabricated from an insulator (e.g., a dielectric) and the metal spacing rings are fabricated from a conductor (i.e., one or more metals, an alloy, or the like), dielectric ring 320 has a higher permittivity than metal spacing rings 310 and 311. Thus, dielectric ring 320 has a greater RF impedance than metal spacing rings 310 and 311. As a result, substantially higher current density will exist in the volume above metal spacing rings 310 and 311 than above dielectric ring 320.

As a result, particles in chamber 15 tend to congregate over dielectric ring 320. In effect, surrounding dielectric ring 320 with low permittivity materials (e.g., metal spacing rings 310 and 311) creates an electropotential well in the volume above dielectric ring 320 by surrounding the low current density in the volume over dielectric ring 320 with high current density in the volumes above metal spacing rings 310 and 311. It is this effect which enhances the trapping of particles (e.g., particles 300) in that volume. The aforementioned current flows create electrostatic forces (substantially in the horizontal direction) which are balance by the electrostatic repulsion of the particles from each other due to their slight negative charges. In the vertical direction, electrostatic and gravitational forces balance, bounding the volume from above and below. The effects of these forces result in the formation of a ring (or multiple concentric rings) of particles above dielectric ring 320.

More broadly, a variety of discontinuities in the surfaces materials presented to the plasma may cause disturbances sufficient to create the requisite field. Thus, the electric field of the present invention may be created by steps, gaps or other such discontinuities designed into either electrode (although the lower electrode is preferable), as well as combinations thereof.

The method and apparatus illustrated in FIGS. 3A and 3B has at least two advantages. First, a technique based on creating a disturbance in the plasma using a discontinuity in one of the electrodes has the advantage of being "self-powered," in that energy from the plasma is used to create the electric field which concentrates the particles. Second, the embodiment of the present invention is relatively simple, the use of which requires only mechanical alterations of one electrode and the chamber wall. This method allows for the control of the horizontal positioning of particles 300 via alterations in the diameter of dielectric ring 320. However, this method provides only limited control over the vertical positioning of particles 300. As a result, particles 300 may be concentrated nearer to substrate 305 than might otherwise be desirable.

Figure 4A:
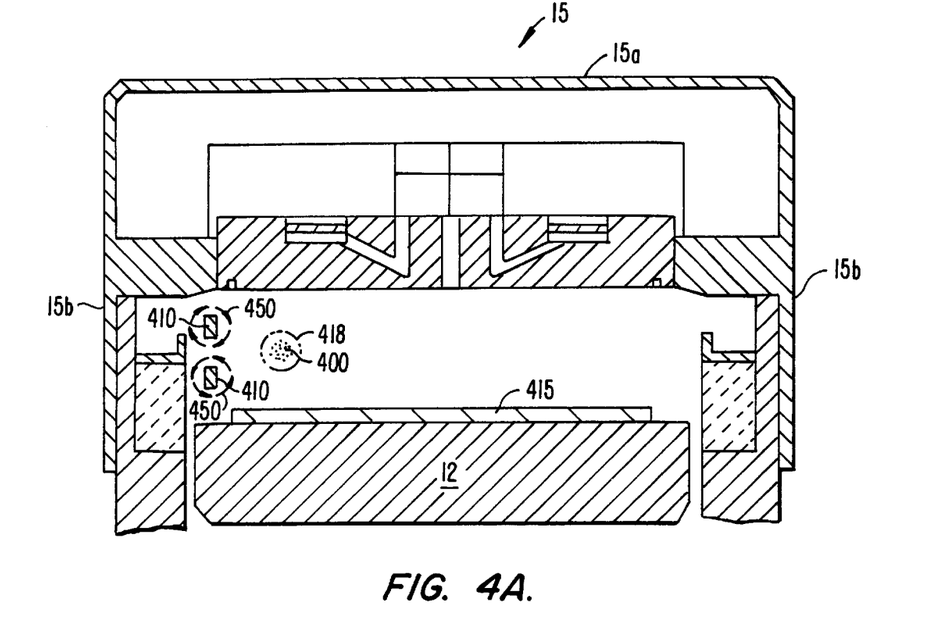
FIG. 4A is a simplified side view of a laser light-scattering particle monitor employing another embodiment of the present invention to improve the monitor's sensitivity.
Figure 4B:
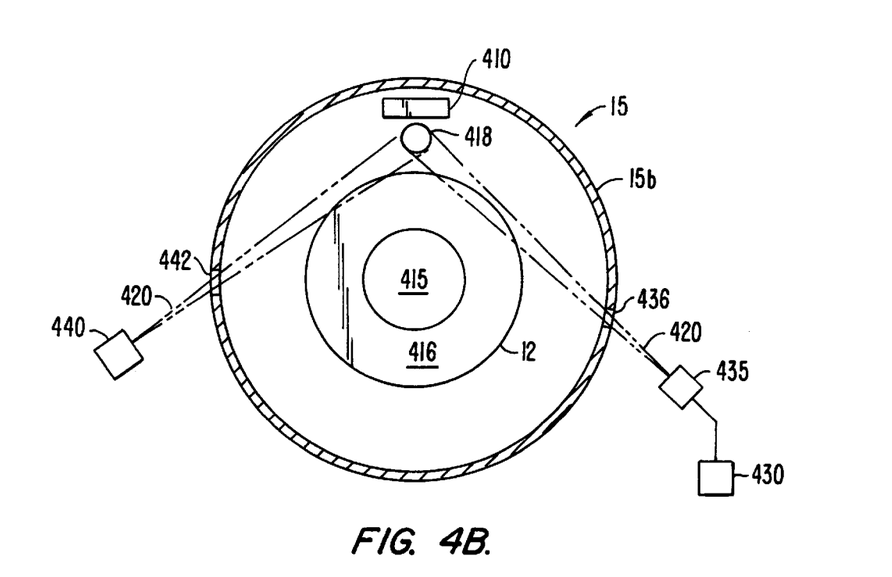
FIG. 4B is a simplified top view of a laser light-scattering particle monitor employing another embodiment of the present invention to improve the monitor's sensitivity.

FIGS. 4A (side view) and 4B (top view) illustrate an alternative embodiment of the present invention that provides a greater degree of control. This embodiment improves the sensitivity of an in situ light scattering technique by increasing the density of particles 400 in a plasma (not shown) in chamber 15 (of FIGS. 1A and 1B) using a magnetic field generated powered by an external power source. Again, particles 400 accumulate a slight negative charge due to their immersion in the plasma. In this embodiment, a toroidal magnet 410 is used to generate a magnetic field above a substrate 415 resting on pedestal 12. The magnetic field concentrates particles 400 in a volume smaller than they would otherwise occupy, which is indicated in FIG. 4 as a reduced volume 418 located along a light path 420. However, any magnet capable of generating a magnetic field sufficient to concentrate particles 400 into reduced volume 418 may be employed. Thus, toroidal magnet 410 may be a permanent magnet, an electromagnet, or other source of magnetic energy.

A laser 430 supplies laser light to a scanner 435, which directs the laser light along light path 420 and through a first window 436 in chamber wall 15b. A photosensor apparatus 440 receives light scattered off of particles 400 through a second window 442. While toroidal magnet 410 is shown as being in the shape of a toroid, other magnet shapes may be used, such as square or rectangular. Additionally, multisegment magnets may also be employed.

Again, particles 400 can be concentrated using such methods because of the slight negative charge they posses. Toroidal magnet 410 creates a magnetic field 450 that acts on particles 400, drawing them into reduced volume 418. The interaction between particles 400 in a magnetic field 450 is described by the Lorentz equation, which describes the force on a moving charged particle in the presence of a magnetic and electric field (e.g., the individual particles of particles 400). This equation may be written as:

$$\vec{F} = m \cdot \frac{d\vec{V}}{dt} = q\left(\vec{E} + \vec{V} \times \vec{B}\right) \quad (1)$$

where F is the force on the particle, V is the particle's velocity, q is the particle's charge, E is the electric field, and B is the magnetic field. This is a vector equation because E, V, B, and F are vector quantities. First, the quantity qE is a vector that is parallel to the field E. The positive sense of the E vector points from the positively charged source of the field to the negatively charged source. The product qE then indicates that a positively charged particle experiences a force, parallel to E, tending to push it from the positive field source to the negative field source. A negatively charged particle (e.g., particles 400) experiences a force –qE (q is negative), which is equal in magnitude but opposite in direction.

The magnetic force is given by qV×B, and is directed such that it is mutually perpendicular to V and B. The positive sense of the magnetic force is, by convention, the direction in which a right hand screw would advance if this screw were turned in a manner that would rotate V to be parallel to B. Another aspect of this force is that when V is parallel to B, then the magnetic force is zero. The force maximizes when V is perpendicular. Its magnitude is given by:

$$|\vec{F}|=|\vec{V}||\vec{B}|\sin\theta \quad (2)$$

where A is the included angle between V and B. From this equation, it is apparent that a charged particle moving parallel to a magnetic field experiences no force from this field. Indeed, if a charged particle moves with velocity V into a magnetic field at some arbitrary angle, then only the component of the velocity that is perpendicular to the field (V) interacts with the this field. The parallel velocity component (V) is unaffected. The simplest case of a magnetic interaction, therefore, consists of a charged particle moving into a constant, uniform magnetic field, having a velocity V such that it is moving at right angles to the field. Negatively charged particles (e.g., particles 400) experience a force that is always perpendicular to V and directed in the negative sense, thus inducing a circular motion. The radius described by the particle is known as the radius of gyration and is determined by equating the magnetic force to the centripetal acceleration encountered in such motion, which yields the expression:

$$r_g = \frac{m|\vec{V}_\perp|}{|\vec{B}|} \cdot \frac{c}{Ze} \quad (3)$$

where $r_g$ is the radius of gyration, m is the mass of the particles in grams, |V| is the magnitude of the perpendicular velocity component in cm/s, |B| is the magnitude of the magnetic field in Gauss, Z is the number of electronic charges present, c is the velocity of light in cm/s, and e is the charge of an electron in use statcoulombs. As can be seen, this leads to a small radius of gyration as long as the magnetic field is strong or the velocity is low. For particles of any given size, then, a stronger magnetic field would be expected to yield greater sensitivity of the associated laser light scattering detector. Equation 3 also indicates that the smaller the particle's mass, the smaller the $r_g$ (as it intuitively evident). Thus, the need for greater sensitivity in regard to smaller particles is met by this method, because the smaller the particles, the more concentrated they will become when using the method of the present invention.

While certain embodiments of this method require an external power source and rather extensive modification to the processing chamber (to include the toroidal magnet), the vertical and horizontal positioning of particles 400 can be well controlled. For example, toroidal magnet 410 may be positioned using an adjustable mounting system (not shown). This allows reduced volume 418 to be positioned away from substrate 415, reducing the likelihood of defects caused by the concentration of particles 400 in reduced volume 418.

The method and apparatus of the present invention is not intended to be limited by the specific parameters set forth in the above descriptions. A person of ordinary skill in the art will realize that different field configurations can be used without departing from the spirit of the invention. A variety of substrate processing equipment any benefit from the method of the present invention. Other equivalent or alternative methods of concentrating particles for in situ detection within plasma-based substrate processing equipment according to the present invention will be apparent to those skilled in the art. These equivalents and alternatives are intended to be included within the scope of the present invention.

What is claimed is:

1. An in situ particle monitoring system of monitoring particles in a plasma within a processing chamber of a substrate processing system for processing a substrate, said particle monitoring system comprising:

a particle concentrator for concentrating at least a portion of the particles into a reduced volume which is smaller than an original volume occupied by said particles;

an optically transparent window in a wall of the processing chamber;

a light source for illuminating at least a portion of said reduced volume through said optically transparent window; and an optical detector for detecting at least some light scattered by at least some particles in said at least a portion of said reduced volume and exiting the processing chamber through said optically transparent window.

2. The particle monitoring system of claim 1, further comprising a display for displaying an output of said optical detector.

3. The particle monitoring system of claim 1, wherein said particle concentrator uses a magnetic field to concentrate the particles.

4. The particle monitoring system of claim 1, wherein said particle concentrator uses an electric field to concentrate the particles.

5. The particle monitoring system of claim 4, wherein said electric field is generated by contact between a first material and the plasma, said first material being between a second material and a third material.

6. The particle monitoring system of claim 5, wherein
   said first material is a dielectric material,
   said second material is a conductive material, and
   said third material is a conductive material.

7. The particle monitoring system of claim 1, wherein the particle concentrator concentrates said at least a portion of the particles into said reduced volume which is positioned away from the substrate.

8. An in situ particle monitoring system for monitoring particles in a plasma within a processing chamber of a substrate processing system, said particle monitoring system comprising:

a particle concentrator for concentrating at least a portion of the particles into a reduced volume which is smaller than an original volume occupied by said particles;

first and second optically transparent windows in a wall of the processing chamber;

a light source for illuminating at least a portion of said reduced volume through said first optically transparent window; and an optical detector for detecting at least some light scattered by at least some particles in said at least a portion of said reduced volume and exiting the processing chamber through said second optically transparent window.

9. The particle monitoring system of claim 8, further comprising a display for displaying an output of said optical detector.

10. The particle monitoring system of claim 8, wherein said particle concentrator uses a magnetic field to concentrate the particles.

11. The particle monitoring system of claim 10, wherein said magnetic field is created using a permanent magnet.

12. The particle monitoring system of claim 10, wherein said magnetic field is created using an electromagnet.

13. The particle monitoring system of claim 8, wherein said particle concentrator uses an electric field to concentrate the particles.

14. The particle monitoring system of claim 13, wherein said electric field is generated by contact between a geometrical discontinuity in a metal surface and the plasma.

15. The particle monitoring system of claim 13, wherein said electric field is generated by contact between a dielectric material and the plasma, said dielectric material being laterally surrounded by a conductive material.

16. The particle monitoring system of claim 13, wherein said electric field is generated by contact between a first material and the plasma, said first material being between a second material and a third material.

17. The particle monitoring system of claim 16, wherein
said first material is a dielectric material,
said second material is a conductive material, and
said third material is a conductive material.

18. The particle monitoring system of claim 17, further comprising:
a ring of said second material, disposed concentrically about the substrate;
a ring of said first material, disposed concentrically about said ring of said second material; and
a ring of said third material, disposed concentrically about said ring of said first material.

19. The particle monitoring system of claim 18, wherein a permittivity of said first material is lower than a permittivity of said second material and a permittivity of said third material.

20. A method for detecting particles using a particle concentration monitor having improved sensitivity, the particle concentration monitor having a light source for creating a light field and a detector having a field of view, for monitoring particles within a processing chamber of a substrate processing system for processing a substrate, said method comprising the steps of:
creating a plasma within the processing chamber, said plasma causing a portion of the particles to acquire a static electrical charge; and
applying an electric field to said portion of the particles to concentrate said portion of the particles within a reduced volume in conformance with said electric field, said reduced volume being smaller than an original volume occupied by said particles and being at least partially within the light field and the field of view.

21. The method of claim 20, further comprising the step of displaying an output of the optical detector.

22. The method of claim 20, wherein said electric field is generated by contact between a dielectric material and said plasma, said dielectric material being laterally surrounded by a metal material.

23. The method of claim 20, wherein said electric field is generated by contact between a geometrical discontinuity in a metal surface and said plasma.

24. The method of claim 20, wherein said reduced volume is positioned away from the substrate.

25. A method for improving the sensitivity of a particle concentration monitor, the particle concentration monitor having a light source for creating a light field and a detector having a field of view, for monitoring particles within a processing chamber of a substrate processing system for processing a substrate, said method comprising the steps of:
creating a plasma within the processing chamber, said plasma causing a portion of the particles to acquire a static electrical charge; and
applying a magnetic field to said portion of the particles to concentrate said portion of the particles within a reduced volume in conformance with said magnetic field, said reduced volume being smaller than an original volume occupied by said particles and being at least partially within the light field and the field of view.

26. The method of claim 25, wherein said magnetic field is created using a permanent magnet.

27. The method of claim 25, wherein said magnetic field is created using an electromagnet.

28. The method of claim 25, wherein said reduced volume is positioned away from the substrate.

29. The method of claim 25, wherein said magnetic field is created by at least one magnet placed inside the processing chamber.

30. A method of monitoring the concentration of particles in a processing chamber of a substrate processing system using a light-scattering particle concentration monitor, the monitor having a light source for creating a light field and a detector having a field of view, said method comprising the steps of:
creating a plasma within the processing chamber, said plasma causing the particles to acquire a static electrical charge;
applying an electric field to the particles to concentrate a first portion of the particles into a reduced volume in conformance with said electric field, said reduced volume being smaller than an original volume occupied by said particles, a portion of said reduced volume being at least partially within the light field and the field of view;
illuminating said portion of said reduced volume using the light source; and
detecting light scattered from particles within said portion of said reduced volume using the detector.

31. A method of monitoring the concentration of particles in a processing chamber of a substrate processing system using a light-scattering particle concentration monitor, the monitor having a light source for creating a light field and a detector having a field of view, said method comprising the steps of:
creating a plasma within the processing chamber, said plasma causing the particles to acquire a static electrical charge;
applying a magnetic field to the particles to concentrate a first portion of the particles into a reduced volume in conformance with said magnetic field, said reduced volume being smaller than an original volume occupied by said particles, a portion of said reduced volume being at least partially within the light field and the field of view;
illuminating said portion of said reduced volume using the light source; and
detecting light scattered from particles within said portion of said reduced volume using the detector.

* * * * *